(12) United States Patent
Whitaker

(10) Patent No.: US 9,184,822 B2
(45) Date of Patent: Nov. 10, 2015

(54) MEDICAL APPARATUS AND METHODS INCLUDING AN ARRAY SYSTEM FOR SEGMENTING SIGNALS AND GENERATING A COMPLEX WAVEFORM AT A FOCAL POINT USING RECOMBINATION OF SEGMENTED SIGNALS

(71) Applicant: The United States of America as represented by the Secretary of the Navy, Washington, DC (US)

(72) Inventor: George Whitaker, Bloomington, IN (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/501,901

(22) Filed: Sep. 30, 2014

(65) Prior Publication Data

US 2015/0055734 A1 Feb. 26, 2015

Related U.S. Application Data

(63) Continuation-in-part of application No. 14/053,883, filed on Oct. 15, 2013, now Pat. No. 8,908,801.

(60) Provisional application No. 61/713,665, filed on Oct. 15, 2012.

(51) Int. Cl.

| H04L 27/00 | (2006.01) |
| H04B 7/06 | (2006.01) |
| H04B 11/00 | (2006.01) |
| H01Q 21/22 | (2006.01) |
| H01Q 3/26 | (2006.01) |
| A61B 6/00 | (2006.01) |
| A61B 5/00 | (2006.01) |
| A61B 5/05 | (2006.01) |

(52) U.S. Cl.
CPC ............... *H04B 7/0617* (2013.01); *A61B 5/05* (2013.01); *A61B 5/726* (2013.01); *A61B 6/00* (2013.01); *H01Q 3/2605* (2013.01); *H01Q 21/22* (2013.01); *H01Q 21/225* (2013.01); *H04B 11/00* (2013.01)

(58) Field of Classification Search
CPC ........... H04L 1/06; H04L 2025/03414; H04L 2025/03426; H04B 7/0697; H04B 7/12
USPC .................................................. 375/267, 299
See application file for complete search history.

(56) References Cited

U.S. PATENT DOCUMENTS

| 6,356,555 B1 * | 3/2002 | Rakib et al. .................... 370/441 |
| 2002/0010544 A1 * | 1/2002 | Rudow et al. ................. 701/213 |
| 2012/0207195 A1 * | 8/2012 | Kawasaki et al. ............. 375/219 |

* cited by examiner

*Primary Examiner* — Don N Vo
(74) *Attorney, Agent, or Firm* — Christopher A. Monsey

(57) ABSTRACT

An apparatus and methods are provided to realize an input waveform using wavelet processing and reconstruction via separated antenna array systems having different beam paths and different frequency components which can include phased array transmitters to recreate the input waveform in medical applications. One aspect of the invention can include a wavelet function used for the examples shown herein which includes a first and second moments of a statistical function, i.e. the mean and variance used with an inverse wavelet to create rectangular pulses that lend themselves to use in the invention herein. Other embodiments of the invention can use other input waveform separation functions paired with signal separation and recombination at a focus point. A selected function can be matched to its application associated with avoidance of sending the input waveform along a single beam path, a desired a focus point, and separation of an input signal.

8 Claims, 9 Drawing Sheets

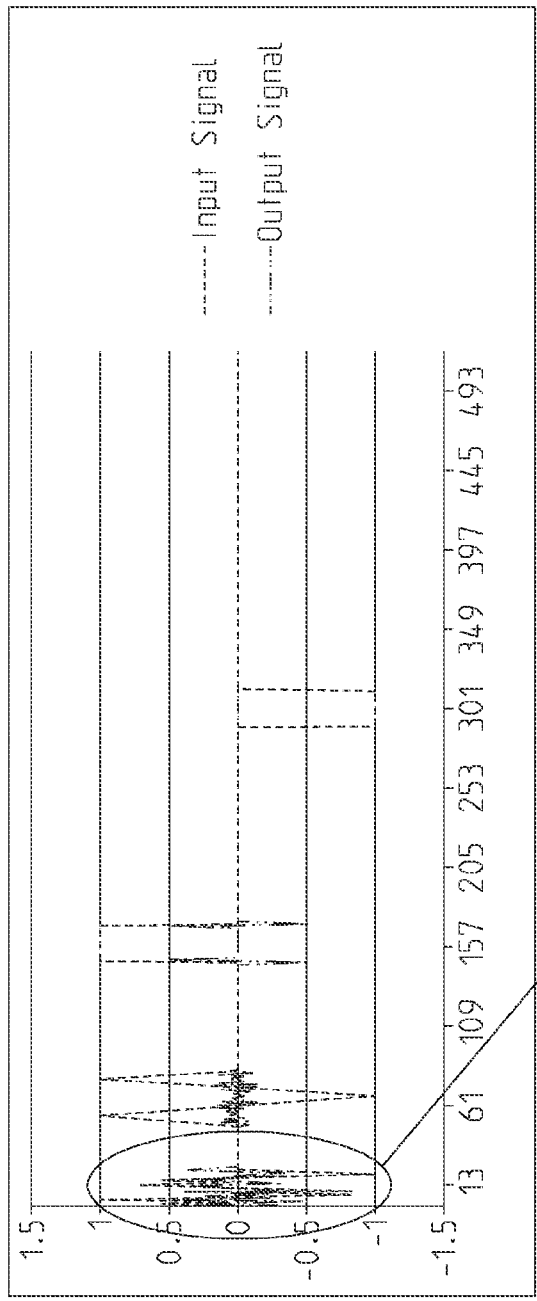
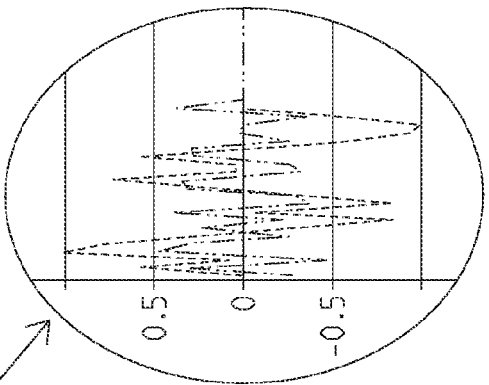
Fig. 3B
Fig. 3B1

MEDICAL APPARATUS AND METHODS INCLUDING AN ARRAY SYSTEM FOR SEGMENTING SIGNALS AND GENERATING A COMPLEX WAVEFORM AT A FOCAL POINT USING RECOMBINATION OF SEGMENTED SIGNALS

CROSS-REFERENCE TO RELATED APPLICATIONS

The present application claims priority to U.S. patent application Ser. No. 14/053,883 filed Oct. 15, 2013 entitled "ARRAY SYSTEM FOR SEGMENTING SIGNALS AND GENERATING A COMPLEX WAVEFORM AT A FOCAL POINT USING RECOMBINATION OF SEGMENTED SIGNALS" which claims priority to U.S. Provisional Patent Application Ser. No. 61/713,665, filed Oct. 15, 2012, entitled "WAVELET RECONSTRUCTION TO REALIZE ARBITRARY WAVEFORM," the disclosures of which are expressly incorporated by reference herein.

STATEMENT REGARDING FEDERALLY SPONSORED RESEARCH OR DEVELOPMENT

The invention described herein was made in the performance of official duties by employees of the Department of the Navy and may be manufactured, used and licensed by or for the United States Government for any governmental purpose without payment of any royalties thereon. This invention (Navy Case 200,080) is assigned to the United States Government and is available for licensing for commercial purposes. Licensing and technical inquiries may be directed to the Technology Transfer Office, Naval Surface Warfare Center Crane, email: Cran_CTO@navy.mil.

BACKGROUND AND SUMMARY OF THE INVENTION

The present invention relates to an apparatus designed to produce focused energy, where a waveform needs to be produced, that is difficult to produce using conventional techniques or if the waveform needs to be produced at a specific location in space. Different portions of the signal can be produced from antennas in physically different locations, all focused to the desired location thereby recreating the original waveform at the desired location. Medical applications include providing a less harmful individual waveform through particular biological structures such as organs (e.g., eyes) which have sensitivity to transmitted energy such as radio frequency energy. Also, an embodiment of the invention permits generating different portions of an input signal along different signal paths so as to avoid specific biological structures such as using directional antennas which generates a complex and/or higher energy combined signal at a focal point e.g., a tumor. One or more directional antennas can be positioned and oriented along specific paths based on characteristics of biological structures along potential beam paths. An embodiment of the invention can also include systems which determine alternative configurations such as beam paths as well as adjustments or substitutions of beam path, waveforms, energy levels, or portions of transmitted signals based on decision engines which could include expert systems for evaluating different configurations of the invention with respect to a set of variables that are predetermined as well as input either manually or as a result of automation such as pattern recognition systems from an initial scan that correlates scan results with patterns associated with biological structures e.g., heart, eyes, lungs, tumors, etc. Variables and decision engines can include, for example, look up tables comprising data associated with organic or biological structures, harm arising to such structures from particular combinations or configurations of an embodiment of the invention, e.g., transmitters, waveforms, energy or intensity, type of emission (e.g., RF or ultrasonic), beam paths, focal points, types of effects desired (e.g., destruction or alteration of a type of biological structure e.g., tumor from application of an embodiment of the invention e.g., combination of signal portions at the focal point).

One exemplary aspect of the invention permits use of an arbitrary signal for communication, interrogative, identification, disruption, jamming, deception, etc. that can be created at a specific location such as in the path of an oncoming threat, at a receiving antenna, or at another specified location. An exemplary system can produce individual signals that are used to create such an arbitrary signal, which can come from different source locations or from a single wide band source. In communications, if a complete signal is created at a transmitting antenna then broadcast to a receiving antenna, the complete signal can be intercepted anywhere in between the transmitting and receiving antennas. With this technique, portions of the desired signal can be created using different transmitting antennas and all focused to a point at or near the receiving antenna where the desired complete signal is combined and created from the different signals originating from the different antennas along different propagation paths. One aspect of the invention can create a signal, which is being protected from interception by virtue of the fact that it does not exist in a complete form, anywhere between the transmitting and receiving antenna. The desired signal only exists at or near the receiving antenna. Another aspect of the invention permits use of a deceptive target, which can be generated in front of an oncoming threat to guide it away, such as unauthorized users who are seeking to intercept data at a department store (e.g., hand-held bar code scanner with Wi-Fi or Bluetooth transceiver) or Wi-Fi enabled site such as at a coffee house or wireless internet cafe.

Aspects of this invention have wide applications in communications, electronic systems, medical, entertainment, and security. An embodiment of the invention has a capability of creating a variety of arbitrary signals using acoustics, radio-frequency (RF), laser, ultrasonics, electrical, or any other medium to which signal processing techniques can be utilized. This arbitrary signal can be created at a specified point or at a source.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which:

FIG. 3B shows an exemplary waveform of another frequency component [F9] of the FIG. 2 input arbitrary waveform produced by an exemplary wavelet decomposition;

FIG. 3B1 shows an expanded view of the exemplary FIG. 3B waveform showing high frequency content of the FIG. 3B waveform;

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice the invention.

Exemplary apparatuses and methods are provided to realize an arbitrary waveform using signal segmentation scheme, e.g., wavelet deconstruction and reconstruction, via antenna systems, which can include phased array transmitters as well as fractal antennas or spatially separated antennas. One exemplary aspect of the invention can include a wavelet function used for the examples shown herein which includes a first and second moments of a statistical function, i.e. the mean and variance, because the inverse wavelet of this function creates rectangular pulses that lend themselves to use in the exemplary version of the invention herein. Other embodiments of the invention can use other functions (e.g., wavelet lifting functions). A selected wavelet function or transform can be matched to an application e.g., a specific antenna structure or transmission scheme.

Figure 1:
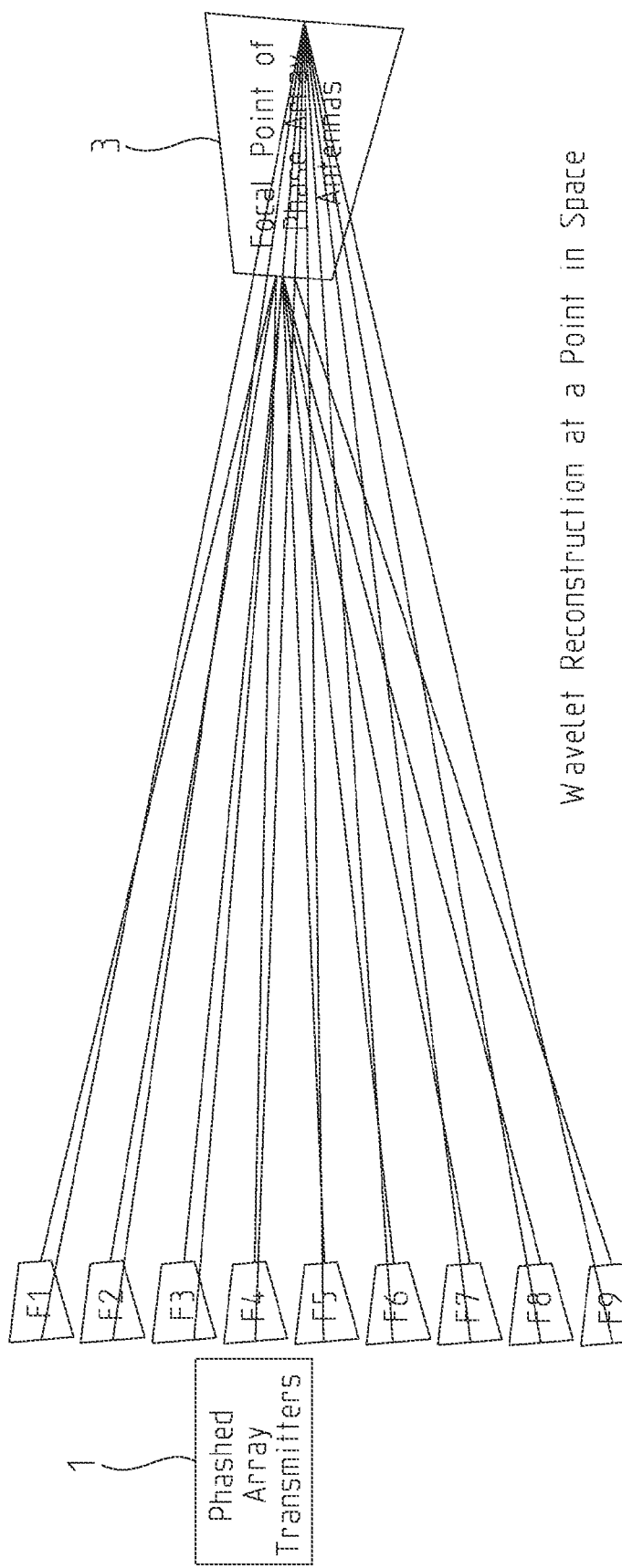
FIG. 1 shows a pictorial of a possible exemplary configuration of phase array antennas to recreate an original input arbitrary signal.

Referring initially to FIG. 1, a possible configuration of phased array antennas 1 to recreate an original input signal in according to one embodiment of the invention is shown. This embodiment provides for combining nine frequencies together, which results in recreation of an original waveform. A number of frequencies can be determined by the number of points in a particular wavelet transform. In other words, a wavelet transform can be selected with specified point transforms. The example shown in FIG. 1 uses nine frequencies (F1, F2, F3, F4, F5, F6, F7, F8, and F9) and is based on an N=9 or 512 point transform. Different portions of the input signal can be produced from antennas in physically different locations where some or all of the antennas are selectively focused using mechanisms such as phased array, spatially oriented arrays, or beam steering to a desired location thereby ensuring any one signal path to a receiving antenna does not have an entire message while recreating the original message's waveform at a desired location. Also, note that each exemplary beam path in this embodiment has a different frequency which adds security as an intercepting party would to have to multiple frequency transceivers to receive all of the different beam path signals.

An embodiment of the invention can also be designed to use a many-to-many transmissions scheme where a modulated waveform is broken into groups of multiple segments such as described herein and those multiple segments are sent to multiple receiving location antennas. Signals received at such multiple locations are then collected and conveyed to collection point for reassembly and recreation of the original message's waveform such as described herein.

An embodiment of the invention can also include one which includes a series of conversions into segmented messages such as described herein which are, for example, transmitted via different frequencies by different separated transmitters to different collection point receivers. Collection point receivers can then in turn covert their received messages into segmented messages such as described herein then transmit the second segmentation of the first segmented messages to a second set of collection point receivers. The second set of collection point receivers can then employ an inverse processing system to reassemble the double segmented original message into the desired re-created complete signal originally segmented and transmitted by different transmitters. In this example, beam steering or phased array systems can also be used to focus or steer signals to a desired reception location. Other types of transmissions systems can include ones such as lasers, focused ultrasonics, multiple types of transmitters or receivers (e.g., mixing differing types of transmitters as well as using spaced apart transmitters/receivers each having a segment of a message), or other means adapted to ensure signals are conveyed primarily to a desired focus location and thereby prevent any one signal path from having a complete message or data transmission from an original message or data stream.

Another embodiment of the invention permits use of multiple transmitters where only some of the transmitters are sending the actual message to a desired recipient point and others are used to generate deception data or diversion signals at specific frequencies or signal paths (e.g., relative bearing to a reception antenna) which are ignored by recipient antenna(s) and not used to recreate an original waveform or signal that has been segmented. In particular, such deception data or diversion signals can be created at a specific location such as in the path of an oncoming threat, at a receiving antenna, or at another specified location.

In some embodiments, some of the transmitters and receivers will transmit on an ongoing basis and others will activate only upon receipt of a predetermined signal. In another embodiment, transmitters and receivers will be grouped into two networks—secure and unsecure. The secure and unsecure systems can both operate in a manner such as described herein however, the secure system network will not transmit or receive until a predetermined authorization, signal or combination of security indicators are received. In both secure and unsecure networks in this embodiment, they will both send segmented messages at different transmission modes (e.g., different frequencies) from different transmission points each with significantly different bearings to a single receiving point or multiple receiving points which receive signals that are separately combined to recreate an original message from the segmented message. However, the each transmitter in the unsecure network exemplary embodiment will constantly or intermittently broadcast and make elements of its presence known to any receiver. Where an attempt to communicate with the unsecure network occurs, then the collected unsecure network can transmit and communicate with the unauthorized recipient who attempted to communicate with the unsecure network and then operate to occupy the attention and focus of the unauthorized recipient. An exemplary system communications used to occupy an unauthorized recipient could include making phony databases available to the unauthorized recipient such as a false credit card database or other "bait" data. The unauthorized recipient will then attempt to use such bait data which will trigger an alarm that the unauthorized user is a threat which will in turn trigger a threat response such as triangulation on the unauthorized receiver's location and dispatch of law enforcement or security forces to deal with the threat.

As another example, an exemplary system can produce individual signals that are used to create a desired arbitrary signal, which can come from different source locations or from a single wide band source which is operating at different frequencies. For example, an exemplary system can use a fractal antenna which has different antenna segments that are fed different segments of an original waveform or modulated data stream for later recombination.

In another example, a Wi-Fi system can be utilized as part of a multiple node system which each transmits and receives a segment of the segmented message created in accordance with an embodiment of the invention. The system can be designed to create overlapping antenna patterns where a predetermined number of Wi-Fi systems are required to transmit all segments of the segmented message. Specific locations can be identified where different antenna patterns overlap to form one or more authorized reception points where a receiving system must be not only located but in communication with multiple Wi-Fi transmitter/receivers in order to receive and transmit all segments of the segmented message.

Another example created in accordance with one embodiment of the invention can receive a request to join or communicate from an unknown user who is not in an overlapping section of the multiple Wi-Fi antennas. The exemplary system can then send a signal to the phased array network comprising a plurality of transmitters in accordance with an embodiment of the invention advising of a request to communication from the unknown user. The network can then communicate with the unknown and potentially unauthorized recipient either using the single Wi-Fi transmitter or use multiple Wi-Fi modes to generate a complete deception waveform at the unknown user's location which is different from the waveforms or transmitted signals used by the Wi-Fi network to communicate with authorized or entitled network which feeds data to the unauthorized recipient and monitors its activity for unauthorized activity. In a case where unauthorized or undesirable activity is detected, then additional security measures can be taken to include offensive or defensive network operations. A deception mode of the system could have a heightened network security system which is either coupled to "bait" data sources or decoupled from sensitive databases or not attached to any sensitive or valuable data sources which could be susceptible to a data collection or other attack.

Figure 2:
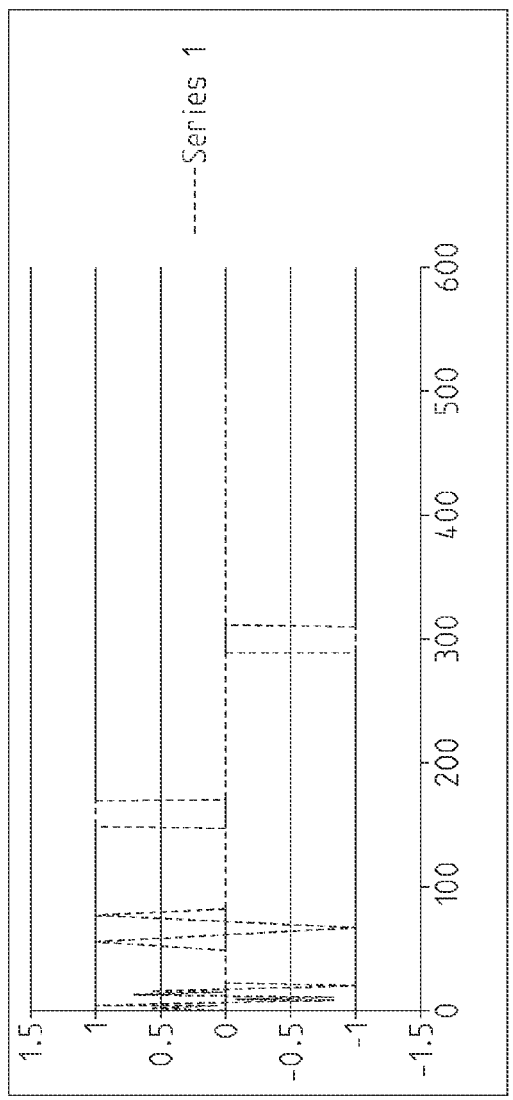
FIG. 2 shows an exemplary input arbitrary waveform in accordance with one exemplary embodiment of the invention.
Figure 3A:
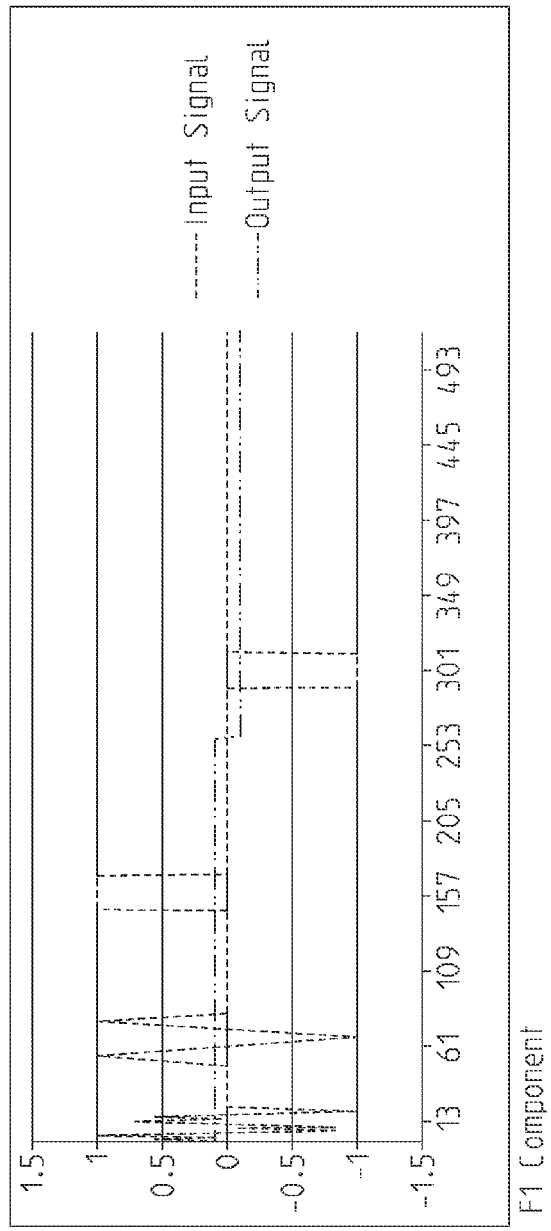
FIG. 3A shows an exemplary waveform of one frequency component [F1] of the FIG. 2 input arbitrary waveform produced by an exemplary wavelet decomposition.
Figure 4:
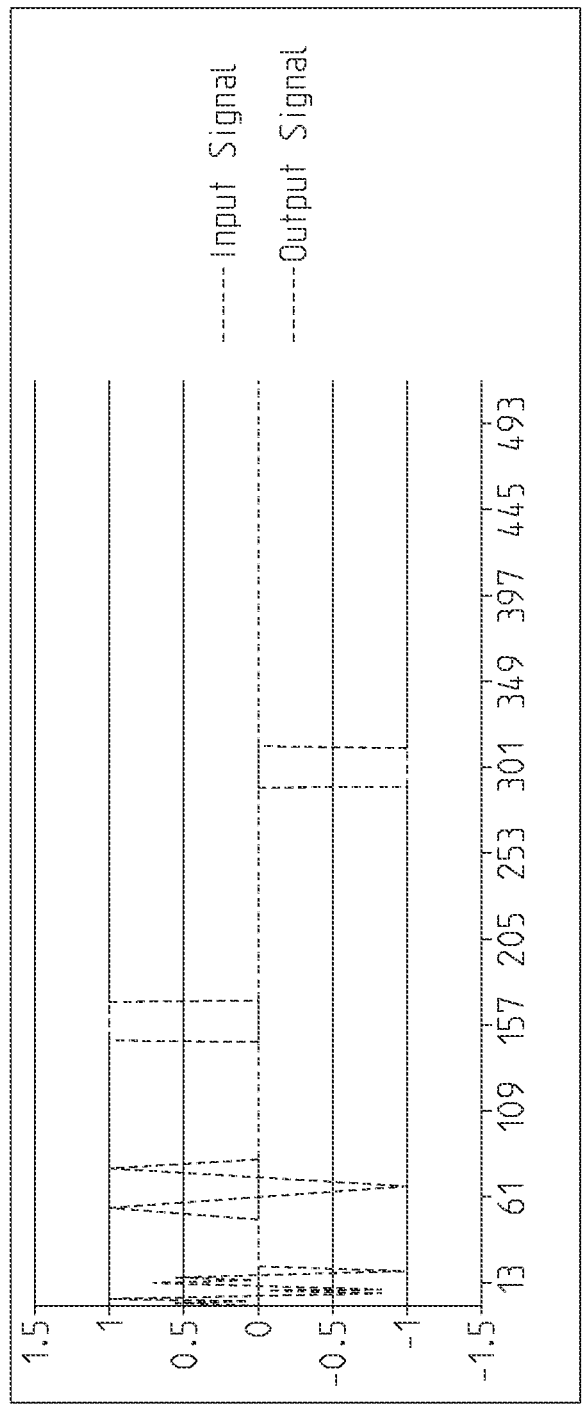
FIG. 4 shows an exemplary waveform of combined frequency components [F1+F2+F3+F4+F5+F6+F7+F8+F9] of the FIG. 2 input arbitrary waveform produced by an exemplary wavelet decomposition embodiment which is reconstructed at a focus point by an array in accordance with one embodiment of the invention such as shown in FIG. 1.

An exemplary system producing output such as shown in FIGS. 2, 3A, 3B, 3B1, and 4, can be designed with a sample rate of 5 µsec or 200 MHz. Based on Nyquist Criteria, 100 MHz is the highest frequency that can be resolved in this embodiment. Thus, F9 is 100 MHz. In a wavelet transform, frequencies are grouped in octaves, thus F8=50 MHz, F7=25 MHz, F6=12.5 MHz, F5=6.25 MHz, F4=3.125 MHz, F3=1.5625 MHz, F2=781.25 KHz and F1=390.625 KHz. The example arbitrary input signal shown in FIG. 2 shows a sinusoidal signal containing multiple frequencies, followed by the beginning of a chirp and then by a positive sequence and a negative sequence with a 25 µsec pulse. FIGS. 2, 3A, 3B, 3B1, and 4 demonstrates exemplary waveforms associated with how an exemplary system shown in FIG. 1 receives an input waveform of FIG. 2, performs wavelet processing, including inverse wavelet transforms, to separate out frequency components of the input waveform, and how an exemplary system combines frequency components to reconstruct aspects of the input waveform signal. In particular, FIG. 2 shows an exemplary input arbitrary waveform used with a system designed in accordance with one exemplary embodiment of the invention. FIG. 3A shows an exemplary waveform of one frequency component [F1] of the FIG. 2 input arbitrary waveform produced by an exemplary wavelet decomposition used with an embodiment of the invention. FIG. 3B shows an exemplary waveform of another frequency component [F9] of the FIG. 2 input arbitrary waveform produced by an exemplary wavelet decomposition. FIG. 3B1 shows an expanded view of the exemplary FIG. 3B waveform showing high frequency content of the FIG. 3B waveform. An exemplary embodiment of the invention generates frequency components F2 through F8 in a similar way as shown in FIGS. 3A and 3B but with different frequency segments. FIG. 4 shows an exemplary waveform of combined frequency components [F1+F2+F3+F4+F5+F6+F7+F8+F9] of the FIG. 2 input arbitrary waveform produced by an exemplary wavelet decomposition embodiment which is reconstructed at a focus point by an array in accordance with one embodiment of the invention such as shown in FIG. 1.

Figure 5:
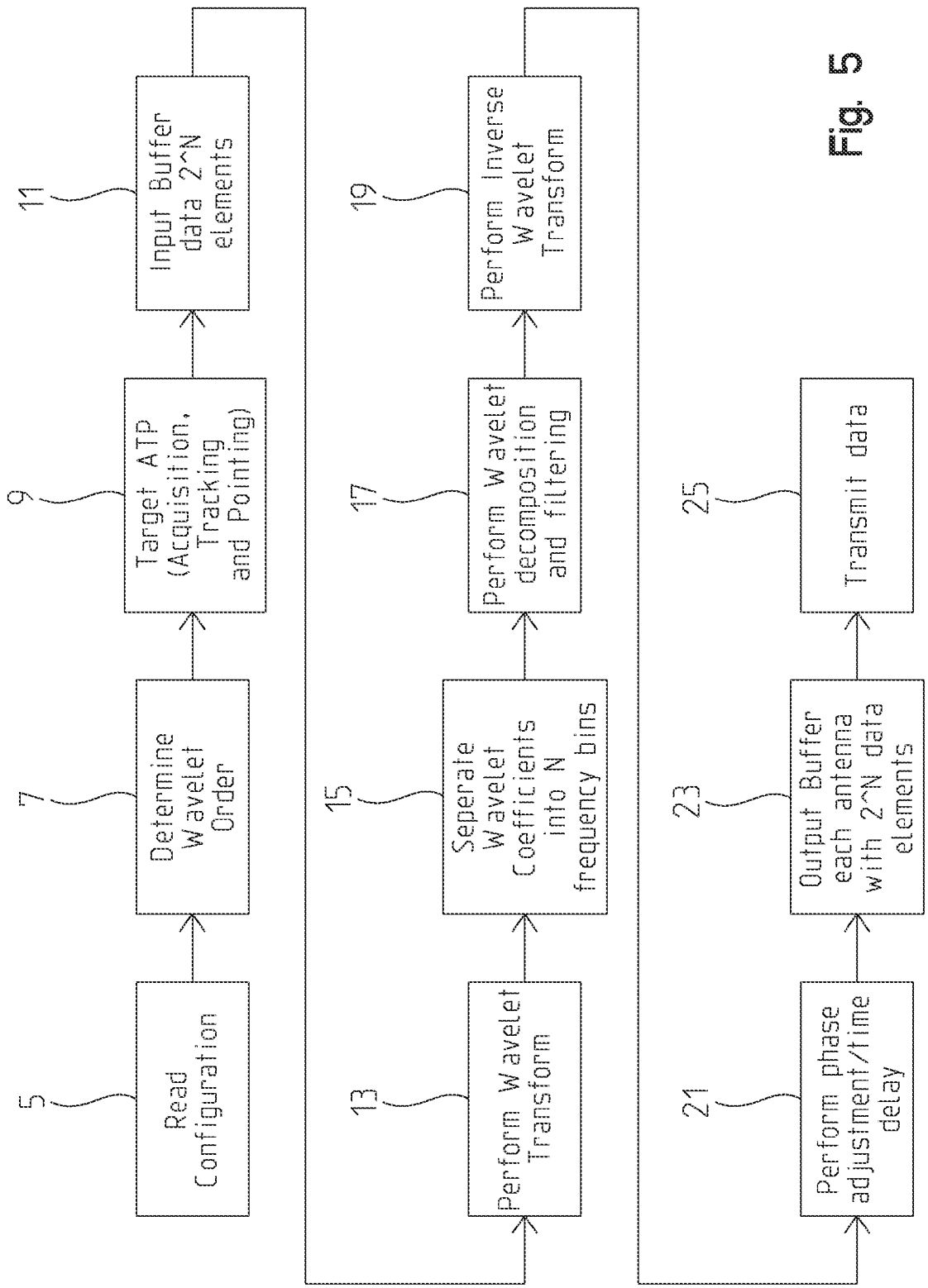
FIG. 5 shows an exemplary high level functional diagram describing blocks or groups of machine readable instructions stored on a machine readable medium.

FIG. 5 shows an exemplary high level functional diagram describing blocks or groups of machine readable instructions stored on a machine readable medium. In particular, an exemplary Read module 5 is provided adapted to read a plurality of data comprising antenna data, location data, pointing vector data, frequency data, and steering data. Data can include real time received from sensors (not shown) or from memory. Data can also include target type as well as data adapted to enable steering of arrays at a stationary or moving target or focus point. A Determine Wavelet Order (DWO) module 7 is adapted to determine how many segments will be used in segmentation of an input signal for processing and transmission. In other words, this exemplary module 7 determines how many frequency bins to store data associated with results from wavelet transform processing. A Target ATP (Acquisition, Tracking and Pointing) module 9 includes machine instructions adapted to receive input from DWO module 7 and a) acquire target location; b) steer antennas to correct pointing vector; and c) track target if moving. An Input Buffer module 11 has machine instructions adapted to receive inputs from Target ATP module 9 and create a buffer with 2^N data elements where N is the Wavelet order (e.g., number of frequency bins) determined in module 7. A Perform Wavelet Transform module 13 has machine instructions adapted to perform wavelet transform processing in accordance with an embodiment of the invention (e.g., based on previous module processing results). A Separate Wavelet Coefficients into N frequency Bins Module (hereinafter Separation Module) 15 includes machine instructions adapted to read wavelet coefficients created in Perform Wavelet Transform module 13 and store resulting data in an interim data structure. A Perform Wavelet Decomposition and Filtering module 17 includes machine instructions adapted to perform wavelet decomposition on results from previous module(s) and apply filtering techniques to resulting decomposed wavelet data associated with each frequency bin. A Perform Inverse Wavelet Transform of N Frequency Bin Separated Signals module 19 includes machine readable instructions adapted to perform inverse wavelet transforms of N frequency bins based on data including data from previous module(s). A Phase Adjustment module 21 includes machine readable instructions adapted to perform phase adjustment/time delay for each data stream associated with each filtered inverse wavelet transform frequency bin depending on configuration and ATP to ensure simultaneous or near simultaneous arrival of all signal transmissions from each transmitters at the target or focus area. Output Buffer module 23 includes processing sequences adapted to ensure each antenna or antenna element transmitting a different frequency bin data stream is supplied with 2^N data elements from respective frequency bin of filtered data. Transmit Data module 25 includes processing sequences adapted to transmit data received from the Output Buffer module 23.

Figure 6:
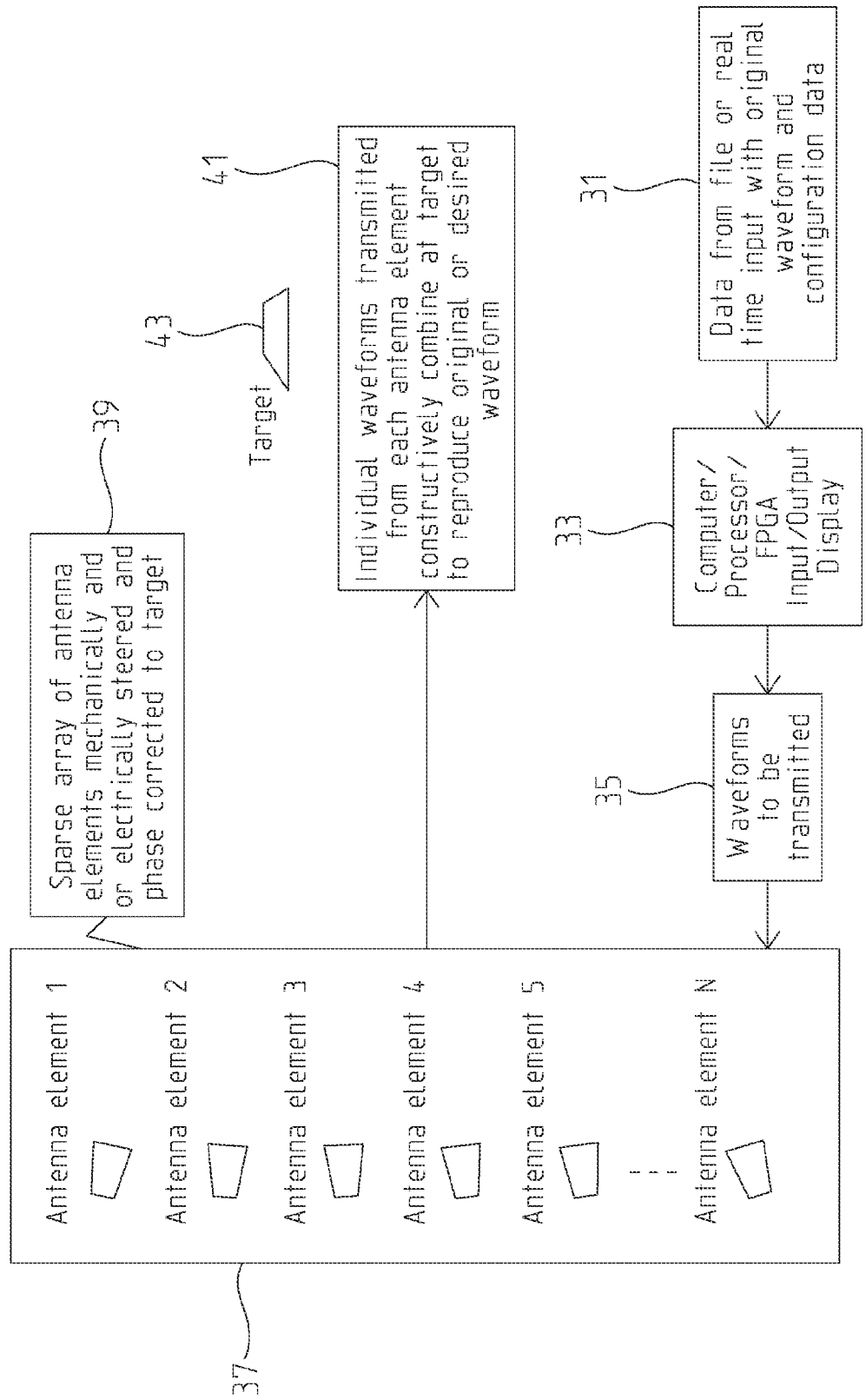
FIG. 6 shows an exemplary functional block diagram of an apparatus or system accordingly to one embodiment of the invention.

FIG. 6 shows an exemplary functional block diagram of an apparatus or system accordingly to one embodiment of the invention. In particular, an exemplary Data File or Real Time input module 31 comprising an original arbitrary waveform or configuration data from a memory storage device or from real time inputs. A Computer/Processor/FPGA Input/Output Display module 33 is provided adapted to read a plurality of data comprising antenna data, location data, pointing vector data. Module 33 would be further adapted to process Data received from module 31 and transform the complete arbitrary waveform into inverse wavelet transforms of N frequency bins forming Waveform to Be Transmitted 35. Antenna Elements 1-N 37 would be configured to be mechanically and/or electrically steered and phase corrected 39 so that the Individual Waveforms Transmitted From Each Antenna Element Would Constructively Combine To Reproduce the Original or Desired Waveform 41 at the target 43 utilizing ATP data from a computer/data processor module 33.

Figure 7:
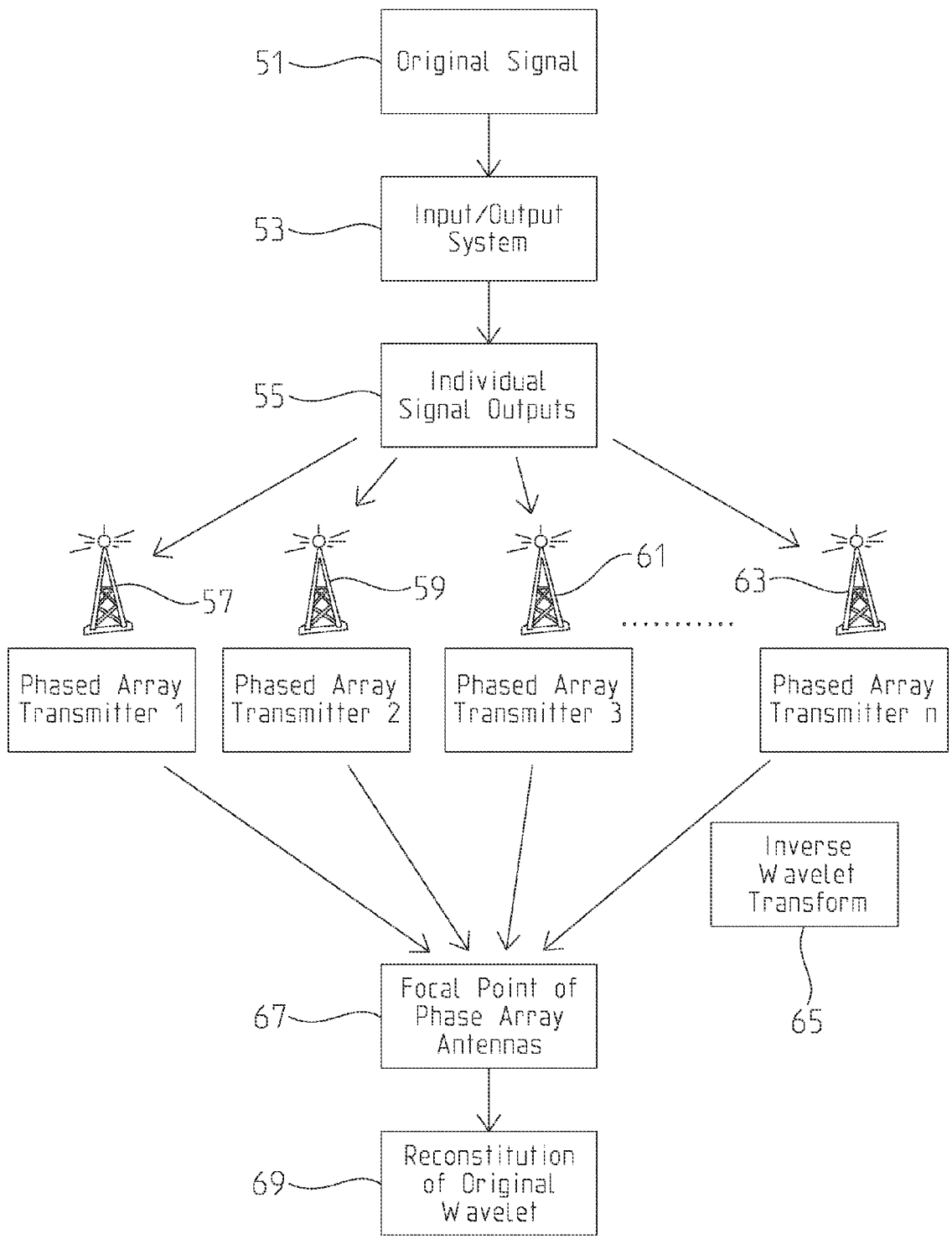
FIG. 7 shows another exemplary functional block diagram of an apparatus or system accordingly to one embodiment of the invention in a larger array system configuration.

FIG. 7 shows another exemplary functional block diagram of an apparatus or system accordingly to one embodiment of the invention in a larger array system configuration. An original signal 51 comprising an original arbitrary waveform or configuration data from a memory storage device or from real time inputs would be passed to an Input/Output System 53 adapted to process the original signal 51 and transform the original signal 51 into inverse wavelet transforms of N frequency bins forming Waveform To Be Transmitted. The individual frequency bins would be transmitted as individual signal outputs 55 to separate phased array transmitters 1-N 57-63. The phased array transmitters 57 would be adapted to direct their individual inverse wavelet transforms 65 utilizing ATP data towards a focal point of phase array antennas 67 far removed from the phased array transmitters 57-63. The focal point of phase array antennas 67 would transmit the incoming inverse wavelet transforms 65 to a Reconstitution of Original Wavelet module 69 adapted to receive the incoming data from the focal point of phase array antennas 67 and either store the data for later reconstitution in a memory storage device or to reconstruct the original wavelet in real time.

Figure 8:
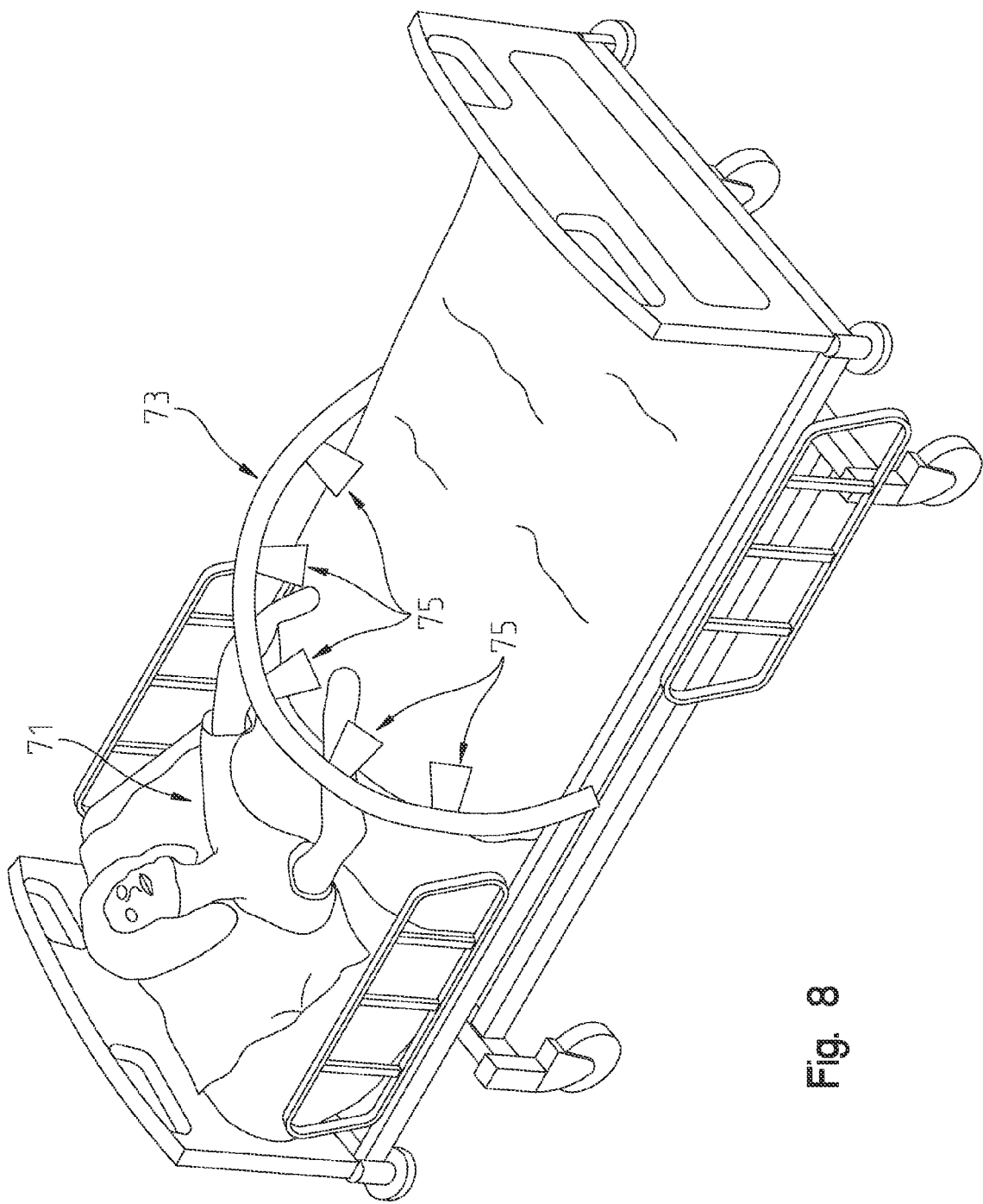
FIG. 8 shows another exemplary functional block diagram of an apparatus or system accordingly to one embodiment of the invention in a medical system application.

FIG. 8 shows another exemplary functional block diagram of an apparatus or system in accordance with another embodiment of the invention. A patient 71 is positioned with respect to an Antenna Array Frame 73 and Array of Transmitters 75 constructed in accordance with one embodiment of the invention. An exemplary Array 75 can be adapted to receive an original first signal and generate multiple outputs (e.g., second signals) which are recombined at a desired area of interest (e.g., focus area) in accordance with an embodiment of the invention where each output has a different electromagnetic (EM) characteristic e.g., radio frequency energy level or intensity which individually are less harmful than the recombined outputs (e.g., recombined original first signal) which are constructively/destructively recombined at the area of interest. A sensor system (not shown) can be adapted to adjust EM characteristics based on tissue which each transmitter array output must pass through in order to minimize damage to tissue along each signal (e.g., second signal) propagation path. Recombined EM energy (e.g., recombined original first signal) can be selected based on a desired effect on tissue or body structures within a focus area of the array where individual transmitter outputs (e.g., second signals) are recombined in accordance with an embodiment of the invention such as discussed above. A sensor system can be used to identify desired tissue or body structures of interest such as tumors (e.g. for destructive application at an area of interest) or other tissue (e.g., muscle tissue for radio frequency or ultrasonic application such as relaxation). For example, a computed tomography (e.g., CT scanner) x-ray system can determine a focus point or target point in a body as well as identifying body tissue along different beam paths associated with different transmitter/antennas (e.g, second signals) used in accordance with an embodiment of the invention. The focus point or target point location where recombined energy, e.g., recombined first signal energy, will be constructively/destructively recombined, can be passed to a Target Acquisition, Tracking, Control, and Pointing (TATCP) system and associated processing sections.

Another embodiment can also include use of the sensor system to analyze and characterize biological structure or body tissues and/or structures along initial beam paths associated with the different transmitter/antennas in a first configuration. Automatic or manual identification of biological structure or body tissues and/or structures that are to be avoided by beam paths can be provided for based on a database of biological structure or body tissues and/or structures that are to be avoided associated with the first configuration's beam paths. A user interface can be provided which permits a user or operator to select or identify structures or tissue to be avoided which are stored by a processing system for automatic avoidance based on characteristics of the structures or tissue or relative location in a body, structure, or tissue. For example, eyes of a person or animal can be designated either in a data store or by a user interface input to be avoided by a beam path in the initial configuration regardless of risk factors.

Pattern recognition systems or databases can be used to perform pattern matching to identify body structures or tissue to be avoided. An eye structure pattern can be included in the pattern recognition system/database which can be correlated to sensor output then automatically identified as a structure or tissue to be avoided with beam paths from transmitter/antennas.

Also, transmitter output and/or beam path can be adjusted based on identified body structure or tissue, frequency, energy, as well as harm or risk associated with the frequency and/or energy. For example, once a body structure or tissue has been identified as associated with an initial configuration beam path and initial transmitter output, then output risk associated with application of the initial transmitter output (such as frequency and/or energy) on the identified body structure or tissue can be determined and compared with a biological risk threshold to determine if the biological risk threshold data value has been exceeded. For example, output risk values associated with the initial configuration beam path and initial transmitter output associated with a particular body structure or tissue (e.g., radio frequency energy above a particular threshold associated with an eye structure or tissue)

can be low, medium, or high. Ranges associated with particular aspects of the transmitters can also be used (e.g., energy values or frequency values). Risk thresholds can be set for each body structure or tissue/tissue type (e.g., organs, brain, nervous system, sensory system, skin, eyes, circulatory system, etc.). For example, an exemplary system can have a risk threshold set e.g., high, medium or low. Accordingly, where the risk threshold has been set for a particular body structure or tissue, e.g., "low" for eye structures, and an initial configuration beam path and initial transmitter output have a medium risk associated with eye structures, then a processing section associated with, e.g., the TATCP, will determine unacceptable risk condition exists for the first configuration and can adjust processing parameters to alter the second signals such as changing antenna's output beam orientation to miss the eyes then recalculating the second signals in accordance with the invention or changing sample rates which changes frequency distribution of a wavelet transform (and therefore alters output frequency of all the transmitters).

Also, a preferential orientation of a transmitter or antenna, energy, or frequency can also be stored with respect to a body structure or tissue based on predetermined risk identifier associated with the body structure or tissue that will have one or more beam paths from the transmitter/receiver passing through it. The first configuration can also include a first configuration of transmitters such as initial orientation of antenna, intensity or energy (e.g. power over time) of output, and/or frequency of output. Once tissues and structures along the initial beam paths have been identified, then the body tissues or structures having a probability of susceptibility to damage from one or more emissions from one or more transmitter/antennas in the first configuration that is higher than a predetermined risk threshold can be identified then the one or more transmitters/antennas can be moved to a second configuration so as to avoid the body tissues or structures having the probability of susceptibility to damage from the one or more emissions from the one or more transmitter/antennas in the first configuration.

An alternative embodiment of the invention can include a system with an electronic protection system designed to address or respond to unauthorized attempts to interfere with a system. Another embodiment can be adapted to respond to other situations where a sender wishes an unauthorized recipient to be confused or to receive incorrect information is desired, a received signal can be processed with a wavelet transform and then altered, if desired, and sent back using this technique to create incorrect signals or signals designed to cause unauthorized or undesirable entities to receive incorrect information.

Another alternative embodiment of the invention can include alternative processing methodology in place of wavelet decompositions described herein such as mathematical decomposition techniques that decomposes an input signal into defined separate signals that constructively sum to recreate the original signal where an approximation of an input signal recreation is acceptable. Exemplary wavelet decompositions are useful as they contain no residual components, thus reducing error. For example, Fourier transforms and power series decompositions can be used, but contain residual errors due to truncation of infinite series. If a sinusoidal signal is used as an input, then a Fourier transform can be used to approximate the original input. For other classes of input waveforms, such as time decay, impulse or polynomial, power series decomposition can be used. Other unique classes of inputs can be more efficiently decomposed by other mathematical processes or transforms.

Figure 9:
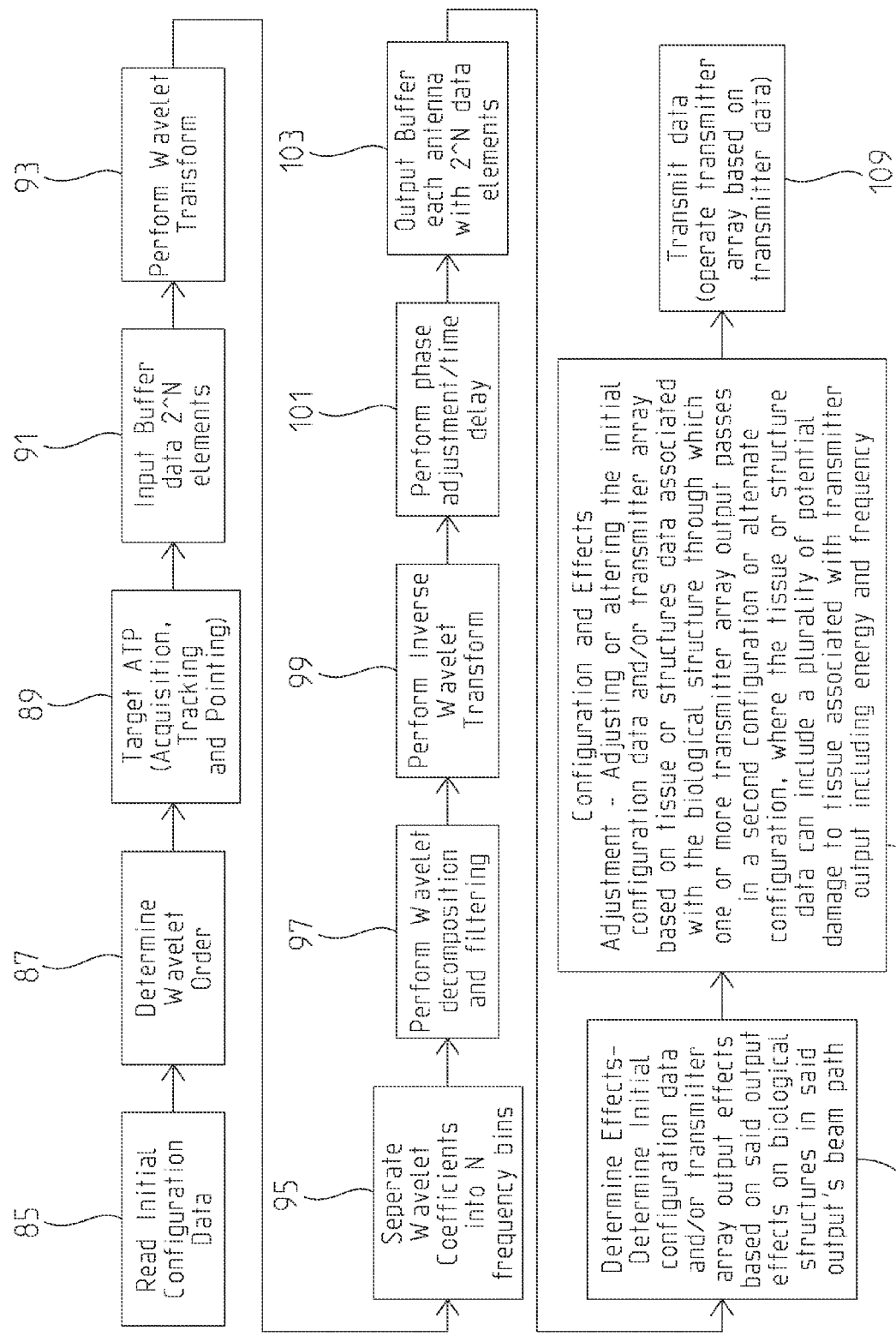
FIG. 9 shows an another exemplary high level functional diagram describing blocks or groups of machine readable instructions stored on a machine readable medium.

Referring to FIG. 9, an exemplary high level functional diagram and processing sequence associated thereto describing blocks or groups of machine readable instructions stored on a machine readable medium is shown. In particular, an exemplary Read module 85 is provided adapted to read a plurality of data comprising antenna data, location data, pointing vector data, frequency data, and steering data. Data can include real time received from sensors (not shown) or from memory. Data can also include target type as well as data adapted to enable steering of arrays at a stationary or moving target or focus point. A Determine Wavelet Order (DWO) module 87 is adapted to determine how many segments will be used in segmentation of an input signal for processing and transmission. In other words, this exemplary module 87 determines how many frequency bins to store data associated with results from wavelet transform processing. A Target ATP (Acquisition, Tracking and Pointing) module 89 includes machine instructions adapted to receive input from DWO module 87 and a) acquire target location; b) steer antennas to correct pointing vector; and c) track target if moving. An Input Buffer module 91 has machine instructions adapted to receive inputs from Target ATP module 89 and create a buffer with $2^N$ data elements where N is the Wavelet order (e.g., number of frequency bins) determined in module 87. A Perform Wavelet Transform module 93 has machine instructions adapted to perform wavelet transform processing in accordance with an embodiment of the invention (e.g., based on previous module processing results). A Separate Wavelet Coefficients into N frequency Bins Module (hereinafter Separation Module) 95 includes machine instructions adapted to read wavelet coefficients created in Perform Wavelet Transform module 93 and store resulting data in an interim data structure. A Perform Wavelet Decomposition and Filtering module 97 includes machine instructions adapted to perform wavelet decomposition on results from previous module(s) and apply filtering techniques to resulting decomposed wavelet data associated with each frequency bin. A Perform Inverse Wavelet Transform of N Frequency Bin Separated Signals module 99 includes machine readable instructions adapted to perform inverse wavelet transforms of N frequency bins based on data including data from previous module(s). A Phase Adjustment module 101 includes machine readable instructions adapted to perform phase adjustment/time delay for each data stream associated with each filtered inverse wavelet transform frequency bin depending on configuration and ATP to ensure simultaneous or near simultaneous arrival of all signal transmissions from each transmitters at the target or focus area. Output Buffer module 103 includes processing sequences adapted to ensure each antenna or antenna element transmitting a different frequency bin data stream is supplied with $2^N$ data elements from respective frequency bin of filtered data. Next, Determine Effects Module 105 determine initial configuration data and/or transmitter array output effects based on said output effects on biological structures in said output's beam path. Configuration and Effects Adjustment Module 107 adjusts or alters the initial configuration data and/or transmitter array (e.g., transmitter output, energy, waveform, beam path(s), etc) based on tissue or structures data associated with the biological structure through which one or more transmitter array output passes in a second configuration or alternate configuration, where the tissue or structure data can include a plurality of potential damage to tissue associated with transmitter output including energy and frequency. Transmit Data module 109 includes processing sequences adapted to transmit data received from the Output Buffer module 103.

Although the invention has been described in detail with reference to certain preferred embodiments, variations and modifications exist within the spirit and scope of the invention as described and defined in the following claims.

The invention claimed is:

1. A medical system including a sensor and signal transmission system comprising:
   a medical support structure operable to support a biological structure and said signal transmission system with respect to a focus point within said biological structure including a first support section and a plurality of second support sections;
   an input device adapted to receive a first plurality of signals comprising an initial input waveform;
   a plurality of spaced apart transmitters;
   a plurality of antenna respectively coupled to said plurality of spaced apart transmitters, wherein each said plurality of antennas are adapted to operate at a different frequency than other said plurality of antennas, each of said plurality of antennas are oriented to have a different beam path through said biological structure than another said transmitter;
   a Target Acquisition, Tracking, Control, and Pointing (TATCP) system adapted to control orientation and operation said plurality of transmitters and antennas, said TATCP system adapted to orient and control said plurality of transmitters and said plurality of antennas;
   a first processing section adapted to read input data comprising antenna data associated with said plurality of spaced apart transmitters, transmitter data associated with said plurality of spaced apart transmitters, target location data, pointing vector data associated with each of said antennas, frequency data associated with said spaced apart transmitters, steering data associated with said transmitters, and target data including a position data of said focus point associated with said target, said processing section is further adapted to communicate said input data to said TATCP system; and
   a second processing section adapted to read at least some of said input data and said initial input waveform and perform signal segmentation, said signal segmentation comprises separating out frequency components of the initial input waveform based on number of said spaced apart antennas, frequencies used by each of said antennas, and wavelet processing, said second processing section is further adapted to sort said frequency components into frequency bins associated with each of said antennas, said second processing section outputs a plurality of second signals to said plurality of spaced apart transmitters comprising said frequency bins and respective said frequency components each saved into each associated said frequency bin;
   a first data storage device adapted to store said plurality of second signals and said input data;
   wherein said TATCP is further adapted to operate said plurality of spaced apart transmitters and focus said plurality of antennas adapted for outputting said second signals at said focus point of said target location based on said input data, said TATCP and said second section is operable to substantially reproduce said first plurality of signals at said target location;
   wherein said TATCP is further adapted to phase correct said plurality of second signals and steer said spaced apart transmitters towards said focal point determined by said TATCP system;
   wherein said TATCP further comprises a third processing section adapted to determine characteristics of said second signals based on selection of second signals' energy and frequency as well as based on a plurality of predetermined biological effects data, said plurality of predetermined effects data including a plurality of potential effects data associated with said tissue or structures in said biological structure within said focus point caused from an initial or subsequent selection of one or more said second signals;
   wherein said TATCP further comprises a fourth processing section adapted to adjust said second signal characteristics based on a first plurality of tissue or structures data associated with said biological structure through which each transmitter array output passes in a second configuration, said first plurality of tissue or structure data further comprising a plurality of potential damage to tissue associated with said transmitter output including energy and frequency.

2. A signal transmission system as in claim 1, wherein said plurality of transmitters and said plurality of antennas are adapted to output one of a group comprising acoustics, radio-frequency (RF), laser, or ultrasonics.

3. A signal transmission system as in claim 1, wherein said plurality of transmitters and said plurality of antennas comprises a focused wide band phased array system.

4. A method of manufacturing a medical application system including a signal transmission system comprising:
   providing a medical support structure operable to support a biological form and said signal transmission system with respect to a focus point including a first support section and a plurality of second support sections;
   providing an input device adapted to receive a first plurality of signals comprising an initial input waveform;
   providing a plurality of spaced apart transmitters;
   providing a plurality of antenna mounted to said plurality of spaced apart transmitters respectively on said plurality of second support sections, said plurality of antenna are respectively coupled to said plurality of spaced apart transmitters, wherein each said plurality of antennas are adapted to operate at a different frequency than other said plurality of antennas, each of said plurality of antennas are oriented to have a different beam path than another said transmitter;
   providing a Target Acquisition, Tracking, Control, and Pointing (TATCP) system adapted to control orientation and operation said plurality of transmitters and antennas, said TATCP system adapted to orient and control said plurality of transmitters and said plurality of antennas;
   providing a first processing section adapted to read input data comprising antenna data associated with said plurality of spaced apart transmitters, transmitter data associated with said plurality of spaced apart transmitters, target location data, pointing vector data associated with each of said antennas, frequency data associated with said spaced apart transmitters, steering data associated with said transmitters, and target data including a position data of said focus point associated with said target, said processing section is further adapted to communicate said input data to said TATCP system;
   providing a second processing section adapted to read at least some of said input data and said initial input waveform and perform signal segmentation, said signal segmentation comprises separating out frequency components of the initial input waveform based on number of said spaced apart antennas, frequencies used by each of said antennas, and wavelet processing, said second processing section is further adapted to sort said frequency components into frequency bins associated with each of said antennas, said second processing section outputs a plurality of second signals to said plurality of spaced apart transmitters comprising said frequency bins and respective said frequency components each saved into each associated said frequency bin;

providing a first data storage device adapted to store said plurality of second signals and said input data;

wherein said TATCP is further adapted to operate said plurality of spaced apart transmitters and focus said plurality of antennas adapted for outputting said second signals at said focus point of said target location based on said input data, said TATCP and said second section is operable to substantially reproduce said first plurality of signals at said target location;

wherein said TATCP is further adapted to phase correct said plurality of second signals and steer said spaced apart transmitters towards said focus point determined by said TATCP system;

wherein said TATCP further comprises a third processing section adapted to determine characteristics of said second signals based on selection of second signals' energy and frequency based on a plurality of predetermined effects data, said plurality of predetermined effects data including a plurality of potential effects data associated with said tissue or structures in said biological structure within said focus point caused from an initial or subsequent selection of one or more said second signals;

wherein said TATCP further comprises a fourth processing section adapted to adjust said second signal characteristics based on a first plurality of tissue or structures data associated with said biological structure through which each transmitter array output passes in a second configuration, said first plurality of tissue or structure data further comprising a plurality of potential damage to tissue associated with said transmitter output including energy and frequency.

5. A method as in claim 4, wherein said plurality of transmitters and said plurality of antennas are adapted to output one of a group comprising acoustics, radio-frequency (RF), laser, or ultrasonics.

6. A method as in claim 4, wherein said plurality of transmitters and said plurality of antennas comprises a focused wide band phased array system.

7. A method of controlling a transmission system associated with a medical application comprising:

providing a medical support structure operable to support a biological structure and said signal transmission system with respect to a target or focus point within said biological structure including a first support section and a plurality of second support sections;

reading a plurality of input data comprising antenna data, location data, pointing vector data, frequency data, and steering data, wherein said input data can include real time received from sensors or from memory, data can also include target type associated with said biological structure as well as data adapted to enable steering of arrays at a stationary or moving target or said focus point;

determining a wavelet order comprising number of segments used in segmentation of an input signal into frequency bins for processing and transmission, wherein the number of segments determines a number of frequency bins;

receiving said plurality of input data and a) acquiring said target at focus point; b) steering a plurality of antennas to a correct pointing vector; and c) tracking said target if said target is moving;

creating a buffer with $2^N$ data elements where N is the wavelet order or the number of frequency bins;

performing wavelet transform processing based on the wavelet order to create a plurality of wavelet coefficient data;

separating and associating the wavelet coefficients with the N frequency bins based on said N frequency bins and reading the wavelet coefficient data to create frequency bin separated and associated wavelet coefficient data;

storing said frequency bin separated and associated wavelet coefficient data into an interim data structure;

performing wavelet decomposition and filtering including performing wavelet decomposition said interim data structure data to produce a plurality of decomposed wavelet data;

applying filtering processing to said plurality of decomposed wavelet data associated with each frequency bin and creating a plurality of filtered decomposed wavelet data;

performing a plurality of inverse wavelet transforms of said filtered decomposed wavelet data comprising performing inverse wavelet transforms of said filtered decomposed wavelet data based on at least N frequency bin data;

performing phase adjustment processing including performing phase adjustment/time delay for a plurality of respective data streams associated with each said filtered decomposed inverse wavelet data based on antenna configuration and inputs from said ATP operable to ensure simultaneous or near simultaneous arrival of all signal transmissions from each said transmitters at said target or focus area;

performing output buffer processing including controlling each antenna or antenna element transmitting a different frequency bin data stream such that said antenna or antenna element is supplied each of the $2^N$ data elements from the respective filtered decomposed frequency bin;

determining characteristics of said signal transmissions based on said signal transmission's energy and frequency based on a plurality of predetermined biological effects data, said plurality of predetermined effects data including a plurality of potential effects data associated with said tissue or structures in said biological structure within said target or focus area caused from an initial or subsequent selection of one or more said signal transmissions;

adjusting one or more said signal transmissions characteristics based on a first plurality of tissue or structures data associated with said biological structure through which each transmitter array output passes in a different configuration of said transmitters comprising orientations of signal transmissions output from one or more said transmitters, said first plurality of tissue or structure data further comprising a plurality of potential damage to tissue associated with said transmitter output comprising one or more said signal transmissions including energy and frequency; and transmitting transmit data received from the output buffer processing using the transmitters and antennas so as to output said signal transmissions from said transmitters in said different configuration.

8. A signal transmission system comprising:
a processor adapted to read and execute non-transitory machine readable instructions;
an input/output section;
a display section adapted to display results from processing associated with said processor and input/output section; and
a machine readable storage medium adapted to store and read said non-transitory machine readable instructions;
wherein said non-transitory machine readable instructions include:
   a first plurality instructions including a data input module adapted to receive and store an input waveform and configuration data, said configuration data comprising antenna data, location data, and pointing vector data;
   a second plurality instructions adapted to receive said configuration data and said input waveform then transform input waveform into inverse wavelet transforms of N frequency bins comprising a waveform to be transmitted;
   a third plurality of instructions adapted to control a plurality of 1-N antenna elements and phase corrected outputs of said antenna elements so that individual waveforms transmitted from each antenna element would constructively combine to substantially reproduce the input waveform at the target location utilizing the configuration data;
   a fourth plurality of instructions operable for determining characteristics of said individual waveforms transmitted from one or more said antenna elements based on said waveform's energy and frequency based on a plurality of predetermined biological effects data, said plurality of predetermined effects data including a plurality of potential effects data associated with said tissue or structures in said biological structure within said target location caused from an initial or subsequent selection of one or more said individual waveforms;
adjusting one or more said signal transmissions characteristics based on a first plurality of tissue or structures data associated with said biological structure through which each transmitter array output passes in a different configuration of said transmitters comprising orientations of signal transmissions output from one or more said transmitters, said first plurality of tissue or structure data further comprising a plurality of potential damage to tissue associated with said transmitter output including energy and frequency.

* * * * *